(12) United States Patent
Ishihara et al.

(10) Patent No.: US 10,772,694 B2
(45) Date of Patent: Sep. 15, 2020

(54) ACTIVATION MEMBER, ACTIVATION MECHANISM, AND METHOD FOR FABRICATING ACTIVATION MECHANISM

(71) Applicant: MEDICAROID CORPORATION, Kobe-shi, Hyogo (JP)

(72) Inventors: Kazuki Ishihara, Kobe (JP); Yu Usuki, Kobe (JP); Kenji Ago, Kobe (JP)

(73) Assignee: MEDICAROID CORPORATION, Kobe-shi (JP)

(*) Notice: Subject to any disclaimer, the term of this patent is extended or adjusted under 35 U.S.C. 154(b) by 71 days.

(21) Appl. No.: 15/962,028

(22) Filed: Apr. 25, 2018

(65) Prior Publication Data

US 2018/0311003 A1    Nov. 1, 2018

(30) Foreign Application Priority Data

May 1, 2017 (JP) .................................. 2017-91234

(51) Int. Cl.
| | | |
|---|---|---|
| *A61B 34/35* | (2016.01) | |
| *A61B 34/00* | (2016.01) | |
| *A61B 17/00* | (2006.01) | |
| *A61B 17/28* | (2006.01) | |
| *A61B 34/30* | (2016.01) | |

(52) U.S. Cl.
CPC ........ *A61B 34/35* (2016.02); *A61B 17/00234* (2013.01); *A61B 17/282* (2013.01); *A61B 34/71* (2016.02); *A61B 2017/00318* (2013.01); *A61B 2017/00367* (2013.01);

(Continued)

(58) Field of Classification Search
CPC ... A61B 34/35; A61B 34/71; A61B 17/00234; A61B 17/282
See application file for complete search history.

(56) References Cited

U.S. PATENT DOCUMENTS

| | | | |
|---|---|---|---|
| 6,394,998 B1 | 5/2002 | Wallace et al. | |
| 10,201,365 B2 * | 2/2019 | Boudreaux | A61B 34/25 |

(Continued)

FOREIGN PATENT DOCUMENTS

| | | |
|---|---|---|
| EP | 1886630 A2 | 2/2008 |
| EP | 1886630 A3 | 3/2008 |

(Continued)

*Primary Examiner* — David M Fenstermacher
(74) *Attorney, Agent, or Firm* — Metrolex IP Law Group, PLLC

(57) ABSTRACT

Disclosed are a compact activation member for operating a medical treatment tool, an activation mechanism having the activation member, and a method for fabricating the activation mechanism. An activation member is directed to an activation member which is provided in a housing as to be rotatable about a rotational axis and around which an elongate element for operating a treatment tool is wound. The activation member includes: a plurality of rotation members which rotate about the rotational axis; and a pressing member which engages with at least one of the plurality of rotation members. Each of the plurality of rotation members includes a surface provided with ridges and grooves. The plurality of rotation members are attached to a base of the housing by being pressed by the pressing member in an extending direction of the rotational axis, with the surfaces of the plurality of rotation members engaged with each other.

12 Claims, 11 Drawing Sheets

(52) U.S. Cl.
CPC ............... *A61B 2017/00477* (2013.01); *A61B 2017/00526* (2013.01); *A61B 2034/305* (2016.02); *A61B 2034/715* (2016.02)

(56) References Cited

U.S. PATENT DOCUMENTS

| | | | |
|---|---|---|---|
| 10,500,002 B2* | 12/2019 | Simaan | A61B 34/30 |
| 2004/0199147 A1* | 10/2004 | Nishizawa | A61B 17/062 |
| | | | 606/1 |
| 2008/0039892 A1* | 2/2008 | Mitsuishi | A61B 34/70 |
| | | | 606/208 |
| 2014/0107665 A1 | 4/2014 | Shellenberger et al. | |
| 2016/0206390 A1 | 7/2016 | Yoshii et al. | |
| 2016/0303743 A1* | 10/2016 | Rockrohr | A61B 17/00234 |
| 2016/0303745 A1* | 10/2016 | Rockrohr | B25J 17/0258 |
| 2017/0007344 A1* | 1/2017 | Seow | A61B 34/71 |
| 2017/0014197 A1* | 1/2017 | McCrea | B25J 15/0226 |
| 2017/0080581 A1* | 3/2017 | Iida | B25J 18/06 |
| 2017/0224367 A1* | 8/2017 | Kapadia | A61B 34/74 |
| 2017/0231653 A1* | 8/2017 | Kapadia | A61B 34/30 |
| | | | 606/208 |
| 2017/0252096 A1* | 9/2017 | Felder | A61B 34/30 |
| 2018/0215051 A1* | 8/2018 | Kan | B25J 9/102 |
| 2019/0117247 A1* | 4/2019 | Kim | A61B 17/29 |
| 2019/0307522 A1* | 10/2019 | Lambrecht | A61B 34/00 |

FOREIGN PATENT DOCUMENTS

| | | |
|---|---|---|
| WO | 2015/080248 A1 | 6/2015 |
| WO | 2015/142958 A1 | 9/2015 |
| WO | 2016/136676 A1 | 9/2016 |

* cited by examiner

US 10,772,694 B2

ACTIVATION MEMBER, ACTIVATION MECHANISM, AND METHOD FOR FABRICATING ACTIVATION MECHANISM

CROSS-REFERENCE TO RELATED APPLICATION

This application claims priority to Japanese Patent Application No. 2017-91234 filed on May 1, 2017, the entire contents of which is incorporated herein by reference.

TECHNICAL FIELD

One or more embodiments relate to an activation member for operating a medical treatment tool, an activation mechanism having the activation member, and a method for fabricating the activation mechanism.

BACKGROUND ART

In recent years, surgical robots have been used in the field of surgery using an endoscope. A surgical robot has a patient-side apparatus which includes a manipulator, and an operating apparatus. An appropriate medical treatment tool is attached to the manipulator. The medical treatment tool is remote controlled by the operating apparatus to carry out surgery.

As an example of such a medical treatment tool used in the surgical robot, U.S. Pat. No. 6,394,998 (Patent Document 1), for example, discloses an activation mechanism that uses a plurality of spools around which a soft member (e.g., wire) is wrapped or unwrapped to move the tip of the tool, such as a grasping forceps.

SUMMARY

Such a surgical robot may need a wide space for installation. Thus, a reduction in size of the surgical robot has been desired. To realize the reduction in size of the surgical robot, a smaller medical treatment tool, which is attached to the distal end of the surgical robot, has been desired.

One or more embodiments are therefore intended to provide a compact activation member for operating a medical treatment tool, an activation mechanism having the activation member, and a method for fabricating the activation mechanism.

To achieve the above objective, an activation member according to one or more embodiments may be directed to an activation member which is provided in a housing so as to be rotatable about a rotational axis and around which an elongate element for operating a treatment tool is wound. The activation member may include: a plurality of rotation members which rotate about the rotational axis; and a pressing member which engages with at least one of the plurality of rotation members. Each of the plurality of rotation members may include a surface provided with ridges and grooves. The plurality of rotation members may be attached to a base of the housing by being pressed by the pressing member in an extending direction of the rotational axis, with the surfaces of the plurality of rotation members engaged with each other.

To achieve the above objective, an activation mechanism according to one or more embodiments may include: a base; a rotation member which rotates about a rotational axis and around which an elongate element for operating a treatment tool is wound; and a pressing member which rotatably fixes the rotation member. The rotation member may be attached to the base via a bearing portion. A length of the bearing portion in an extending direction of the rotational axis may be longer than or equal to one fourth (¼) of a length of the rotation member in said direction.

To achieve the above objective, a method for fabricating an activation mechanism according to one or more embodiments may be directed to a method for fabricating an activation mechanism around which a first elongate element for operating a treatment tool is wound. The method may include: attaching a first rotation member to a base; attaching a second rotation member to the first rotation member such that a rotational axis of the first rotation member and a rotational axis of the second rotation member are aligned with each other; winding the first elongate element around the first rotation member or the second rotation member; and fixing the first rotation member and the second rotation member by a pressing member such that the first rotation member and the second rotation member are rotatable about the rotational axis.

DETAILED DESCRIPTION

[Surgical System]

Figure 1:
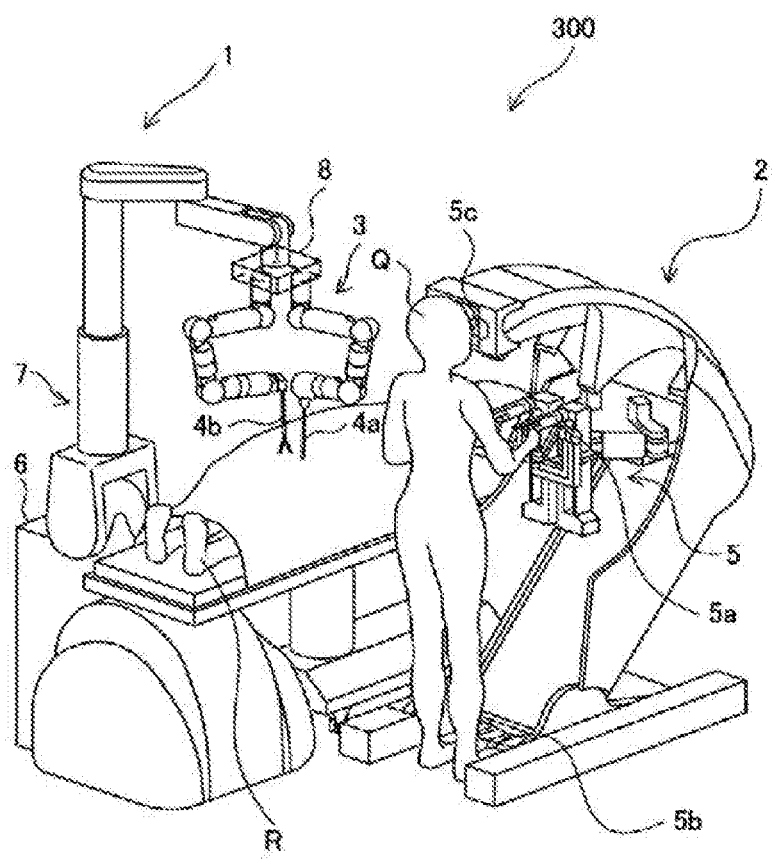
FIG. 1 is a diagram illustrating a configuration of a surgical system of one or more embodiments.

FIG. 1 is a diagram illustrating a configuration of a surgical system of one or more embodiments.

Referring to FIG. 1, a surgical system 300 is used, for example, to carry out a surgical operation on a treatment target R, such as a human or an animal, using an endoscope operated by an operator Q through a patient-side apparatus 1. The surgical system 300 has the patient-side apparatus 1 and an operating apparatus 2 which operates the patient-side apparatus 1.

The operator Q inputs, to the operating apparatus 2, a movement instruction for the patient-side apparatus 1. The operating apparatus 2 transmits an instruction signal which includes this movement instruction to the patient-side apparatus 1. The patient-side apparatus 1 receives the instruction signal transmitted from the operating apparatus 2, and moves an endoscope assembly 4a and a medical treatment tool 4b connected to the distal end of the patient-side apparatus 1, based on the movement instruction included in the instruction signal received.

More specifically, the operating apparatus 2 includes an operation input section 5 which has a control manipulator 5a and an operation pedal 5b, and a monitor 5c which displays an image taken by the endoscope assembly 4a. The control manipulator 5a and the operation pedal 5b are equipment through which the operator Q inputs the movement instruction.

The operator Q operates the control manipulator 5a and the operation pedal 5b to input the movement instruction to the operating apparatus 2, while viewing an image of the target site displayed on the monitor 5c. The operating apparatus 2 transmits the instruction signal, which includes the input movement instruction, to the patient-side apparatus 1 through a wired or wireless connection.

The patient-side apparatus 1 includes: a positioner 7; a platform 8 attached to an end of the positioner 7; a plurality of manipulators 3 detachably attached to the platform 8; the endoscope assembly 4a; the medical treatment tool 4b; and a controller 6 which controls the movement of the patient-side apparatus 1.

The endoscope assembly 4a and the medical treatment tool 4b are attached to the manipulators 3. Examples of the medical treatment tool 4b include a grasping forceps (i.e., a grasper), a needle holder (i.e., a needle driver), and a pair of scissors.

The controller 6 receives the instruction signal transmitted from the operating apparatus 2, and moves the endoscope assembly 4a and the medical treatment tool 4b, based on the instruction signal received.

Specifically, the controller 6 which has received the instruction signal first moves the positioner 7, thereby positioning the platform 8, based on the movement instruction included in the instruction signal. The controller 6 positions the manipulators 3, too, such that the endoscope assembly 4a and the medical treatment tool 4b take predetermined initial positions with respect to cannulas, not shown, retained on the body surface of the treatment target R.

Then, the controller 6 outputs, based on the movement instruction, a control signal for activating the endoscope assembly 4a and the medical treatment tool 4b to the endoscope assembly 4a and the medical treatment tool 4b via the manipulators 3. The endoscope assembly 4a and the medical treatment tool 4b move according to the control signal transmitted from the controller 6.

The controller 6 does not need to be embedded in the positioner 7, and may be provided independently of the positioner 7.

[Medical Treatment Tool]

<General Configuration>

Figure 2:
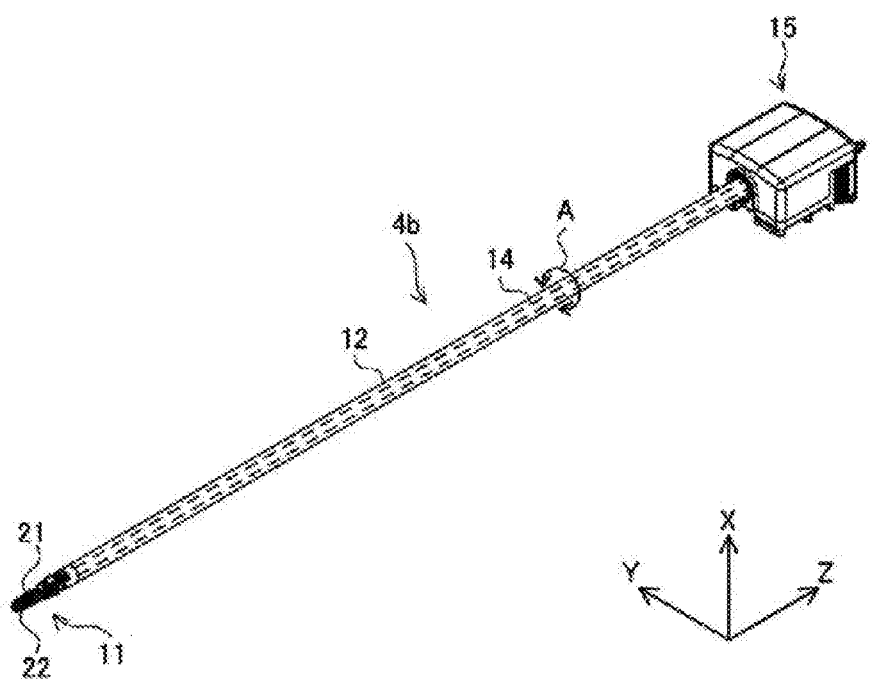
FIG. 2 is a diagram illustrating a configuration of a medical treatment tool of one or more embodiments.

FIG. 2 is a diagram illustrating a configuration of a medical treatment tool of one or more embodiments.

Referring to FIG. 2, the medical treatment tool 4b includes an end portion 11, a shaft 12, an elongate element 14 (e.g., wire or cable) for operating the end portion 11, and an activation mechanism 15 which activates the elongate element 14. Hereinafter, the elongated element 14 will be described, taking wire as an example.

The end portion 11 has two jaws 21 and 22, for example. The two jaws 21 and 22 having the same shape can reduce the fabrication costs. The shaft 12 has a tubular shape extending in the longitudinal direction of the medical treatment tool 4b, and is rotatable in the directions indicated by the arrows A. That is, the shaft 12 is rotatable about its own longitudinal axis.

The wire 14 is made, for example, of tungsten or stainless steel to provide sufficient strength, bendability, and durability. Stainless steel is softer, but stretches more easily, than tungsten. Tungsten is harder, but is less likely to stretch, than stainless steel.

The activation mechanism 15 is mounted on one of the manipulators 3 of the patient-side apparatus 1 illustrated in FIG. 1. The activation mechanism 15 receives the control signal from the patient-side apparatus 1 via the manipulator 3. Based on this control signal, the activation mechanism 15 moves the wire 14 along the longitudinal direction of the medical treatment tool 4b and/or rotates the shaft 12 in the directions indicated by the arrows A. Detailed configurations of the activation mechanism 15 will be described later.

(End Portion)

Figure 3:
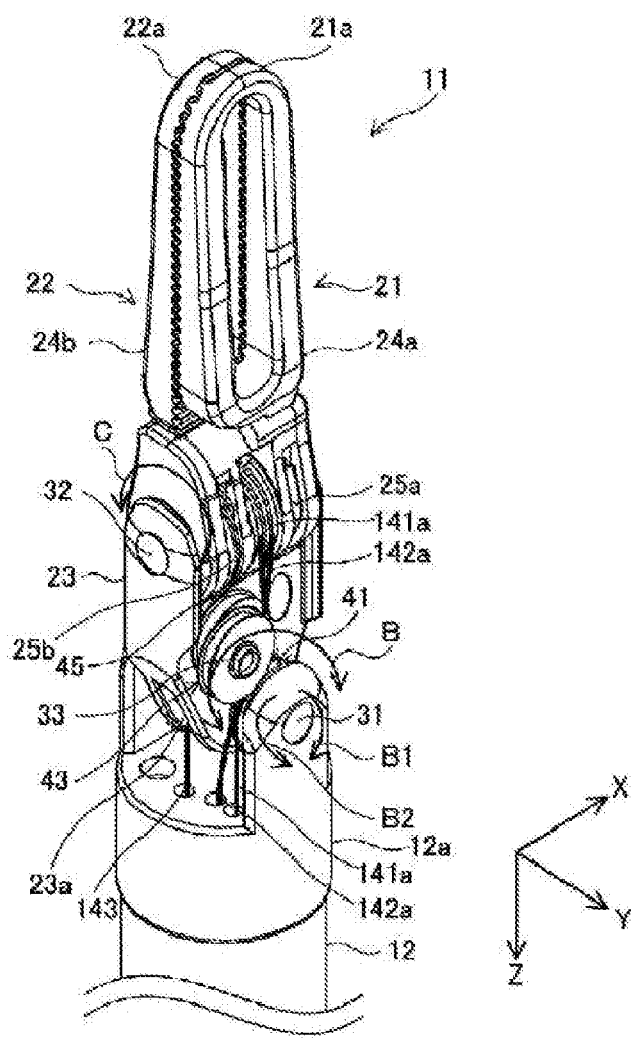
FIG. 3 is a diagram illustrating a perspective view of a configuration of an end portion of the medical treatment tool in FIG. 2.

FIG. 3 is a diagram illustrating a perspective view of a configuration of an end portion of the medical treatment tool in FIG. 2.

Referring to FIG. 3, the end portion 11 also has a wrist portion 23 in addition to the jaw 21 and the jaw 22. The wrist portion 23 is mounted on an end 12a of the shaft 12 via a first connection 31. The wrist portion 23 is pivotable about the first connection 31 in the directions indicated by the arrows B.

The jaws 21 and 22 are mounted on the wrist portion 23 via a second connection 32. The jaws 21 and 22 have finger portions 24a and 24b and pulley portions 25a and 25b, respectively. The finger portions 24a and 24b are pivotable about the second connection 32 in the directions indicated by the arrows C. The pulley portions 25a and 25b are rotatable about the second connection 32.

In one preferred embodiment, the first connection 31 and the second connection 32 extend in different directions. In the present embodiment, the direction in which the first connection 31 extends and the direction in which the second connection 32 extends form a 90 degree angle. In the following description, the direction in which the first connection 31 extends will be referred to as a "Y-axis direction," the direction in which the second connection 32 extends as an "X-axis direction," and the longitudinal direction of the shaft 12 as a "Z-axis direction."

Figure 4:
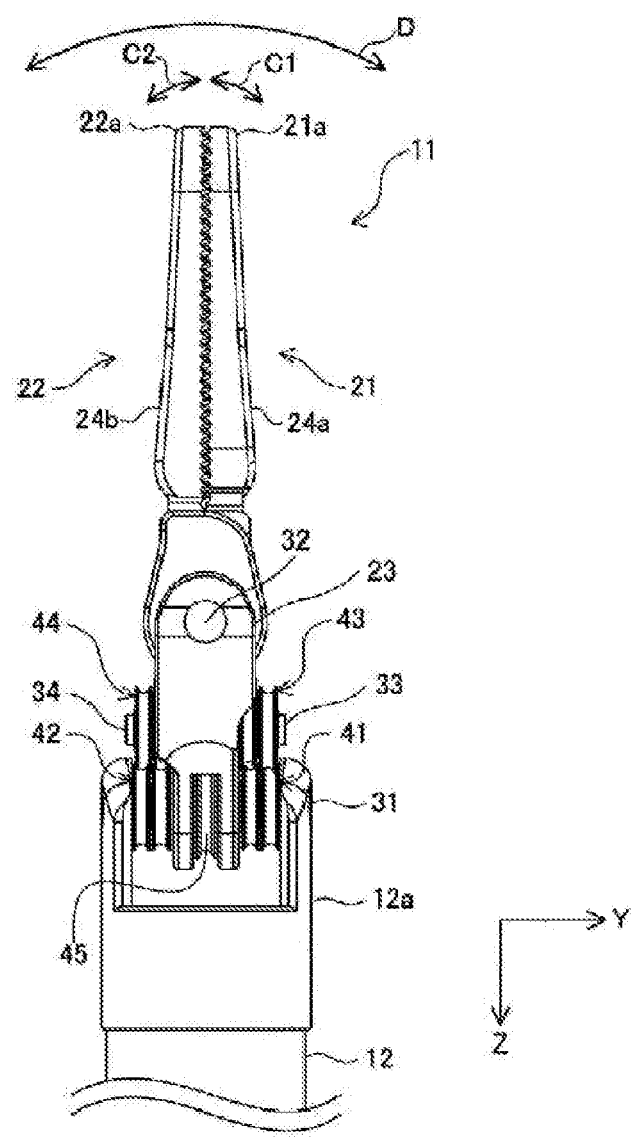
FIG. 4 is a diagram illustrating a side view of the configuration of the end portion of the medical treatment tool in FIG. 2.

FIG. 4 is a diagram illustrating a side view of the configuration of the end portion of the medical treatment tool in FIG. 2.

Referring to FIG. 4, the jaws 21 and 22 have free ends 21a and 22a, respectively. The free ends 21a and 22a pivot about the second connection 32, and thus can move toward and away from each other or can pivot in the same direction, as indicated by the arrows C1 and C2.

The end portion 11 also has a first pulley portion 41, a second pulley portion 42, a third pulley portion 43, a fourth pulley portion 44, and a fifth pulley portion 45 in addition to the jaws 21 and 22 and the wrist portion 23. Each of the first, second, third, and fourth pulley portions 41, 42, 43, and 44 has an inner pulley and an outer pulley.

The first, second, and fifth pulley portions 41, 42, and 45 are mounted on the end 12a via the first connection 31, and are rotatable about the first connection 31. The third pulley portion 43 is mounted on the wrist portion 23 via a third connection 33, and is rotatable about the third connection 33. The fourth pulley portion 44 is mounted on the wrist portion 23 via a fourth connection 34, and is rotatable about the fourth connection 34.

The plane of rotation of the first pulley portion 41 and the plane of rotation of the third pulley portion 43 are present on substantially the same plane. The plane of rotation of the second pulley portion 42 and the plane of rotation of the fourth pulley portion 44 are present on substantially the same plane.

(Wire-Wrapping Around End Portion)

Figure 5:
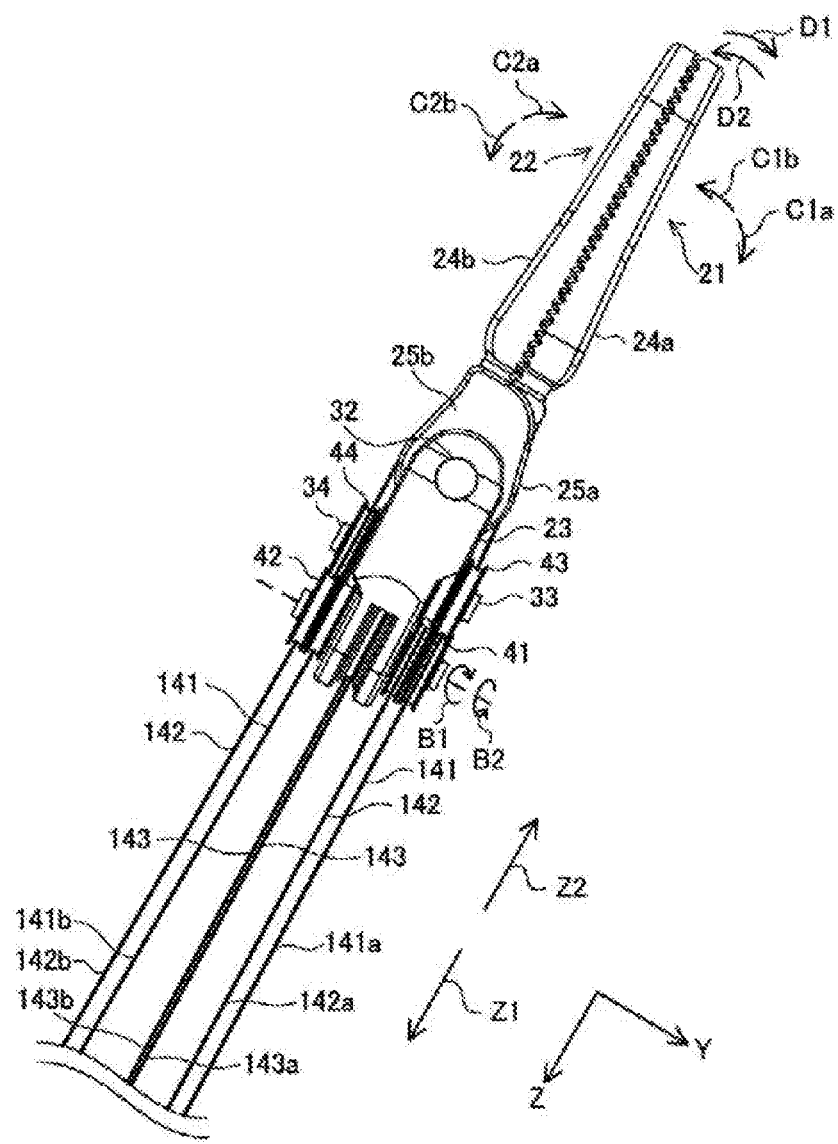
FIG. 5 is a diagram illustrating an example wire-wrapping around the end portion of the medical treatment tool of one or more embodiments.

FIG. 5 is a diagram illustrating an example wire-wrapping around the end portion of the medical treatment tool of one or more embodiments. In FIG. 5, the arrow Z1 indicates the positive direction of the Z-axis extending in the longitudinal direction of the shaft 12, and the arrow Z2 indicates the negative direction of the Z-axis.

In the present embodiment, the medical treatment tool 4b includes three wires 14. The three wires 14 will be referred to as wires 141, 142, and 143. The wires 141, 142, and 143 have first elongate elements 141a, 142a, and 143a and second elongate elements 141b, 142b, and 143b, respectively.

Referring to FIG. 5, the medical treatment tool 4b is assembled as follows: the wire 141 is wrapped around the outer pulley of the first pulley portion 41 and the outer pulley of the third pulley portion 43; the wire 141 is then wrapped around the pulley portion 25b of the jaw 22; and the wire 141 is further wrapped around the inner pulley of the fourth pulley portion 44 and the inner pulley of the second pulley portion 42. Further, the wire 141 is fixed, for example, to a member (not shown) formed at the finger portion 24b of the jaw 22. The jaw 22 therefore moves in conjunction with the movement of the wire 141.

The wire 142 is wrapped around the inner pulley of the first pulley portion 41 and the inner pulley of the third pulley portion 43; the wire 142 is then wrapped around the pulley portion 25a of the jaw 21; and the wire 142 is further wrapped around the outer pulley of the fourth pulley portion 44 and the outer pulley of the second pulley portion 42. Further, the wire 142 is fixed, for example, to a member (not shown) formed at the finger portion 24a of the jaw 21. The jaw 21 therefore moves in conjunction with the movement of the wire 142.

The wire 143 is wrapped around the fifth pulley portion 45. Further, the wire 143 is fixed, for example, to a member (not shown) formed at the wrist portion 23. The wrist portion 23 therefore moves in conjunction with the movement of the wire 143.

(Movement of End Portion)

The first elongate element 141a of the wire 141, when pulled in the Z1 direction, causes the jaw 22 to pivot about the second connection 32 in the direction of the arrow C2a, that is, to pivot circumferentially about the second connection 32 toward the jaw 21. The second elongate element 141b of the wire 141, when pulled in the Z1 direction, causes the jaw 22 to pivot about the second connection 32 in the direction of the arrow C2b, that is, to pivot circumferentially about the second connection 32 away from the jaw 21.

The first elongate element 142a of the wire 142, when pulled in the Z1 direction, causes the jaw 21 to pivot about the second connection 32 in the direction of the arrow C1a, that is, to pivot circumferentially about the second connection 32 away from the jaw 22. The second elongate element 142b of the wire 142, when pulled in the Z1 direction, causes the jaw 21 to pivot about the second connection 32 in the direction of the arrow C1b, that is, to pivot circumferentially about the second connection 32 toward the jaw 21.

The second elongate element 141b and the first elongate element 142a, when simultaneously pulled in the Z1 direction, cause the jaws 21 and 22 to pivot circumferentially about the second connection 32 away from each other. The first elongate element 141a and the second elongate element 142b, when simultaneously pulled in the Z1 direction, cause the jaws 21 and 22 to pivot circumferentially about the second connection 32 toward each other.

The first elongate element 141a and the first elongate element 142a, when simultaneously pulled in the Z1 direction, cause both of the jaws 21 and 22 to pivot circumferentially about the second connection 32 in the direction indicated by the arrow D1. That is, the jaw 21 pivots in the C1a direction, and the jaw 22 pivots in the C2a direction.

The second elongate element 141b and the second elongate element 142b, when simultaneously pulled in the Z1 direction, cause both of the jaws 21 and 22 to pivot circumferentially about the second connection 32 in the direction indicated by the arrow D2. That is, the jaw 21 pivots in the C1b direction, and the jaw 22 pivots in the C2b direction.

The first elongate element 143a, when pulled in the Z1 direction, causes the wrist portion 23 illustrated in FIGS. 3 and 4 to pivot about the first connection 31 in a direction indicated by the arrow B2, that is, to pivot circumferentially about the first connection 31 and counterclockwise as viewed from the positive to negative direction of the Y-axis. The second elongate element 143b, when pulled in the Z1 direction, causes the wrist portion 23 to pivot about the first connection 31 in a direction indicated by the arrow B1, that is, to pivot circumferentially about the first connection 31 and clockwise as viewed from the positive to negative direction of the Y-axis.

In this manner, the jaws 21 and 22 and the wrist portion 23 move independently of one another in conjunction with the movements of the wires 141, 142, and 143.

[Activation Mechanism]

Figure 6:
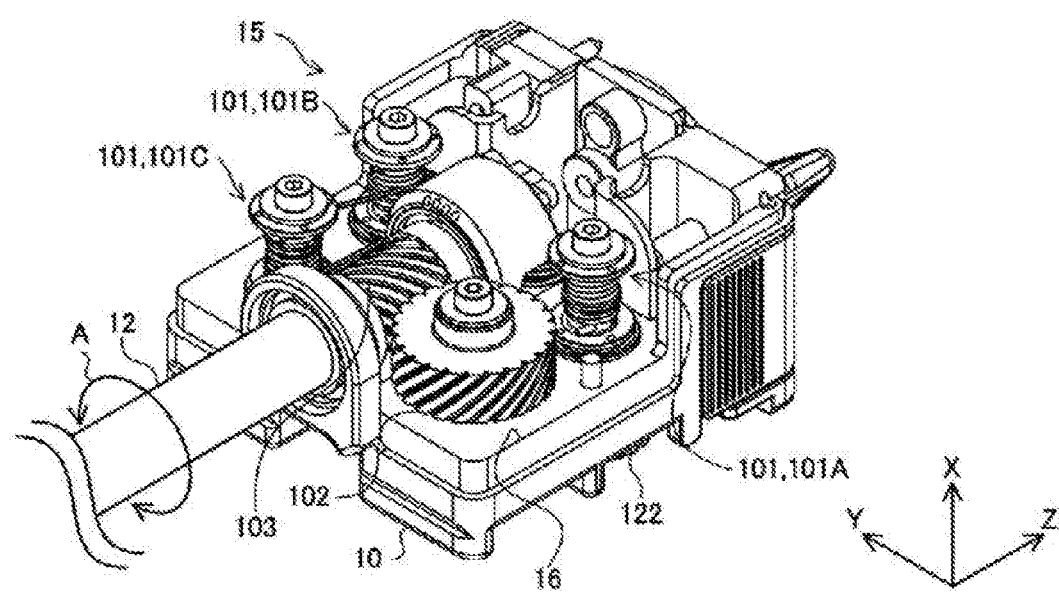
FIG. 6 is a diagram illustrating a perspective view of a configuration of an activation mechanism of one or more embodiments.

FIG. 6 is a diagram illustrating a perspective view of a configuration of an activation mechanism of one or more embodiments.

Referring to FIG. 6, the activation mechanism 15 has a housing 10, a plurality of activation members 101 rotatably provided in the housing 10, a first gear 102 rotatably provided in the housing 10, a second gear 103 which engages with the first gear 102, an activation transmitting system (not shown), and an actuator (not shown). In FIG. 6, an upper portion of the housing 10 is omitted to illustrate an internal configuration of the activation mechanism 15.

The activation transmitting system has a plurality of transmission members which will be described later. Each of the plurality of activation members 101 and the first gear 102 has a receiving member 122. Each of the plurality of transmission members engages with a corresponding one of these receiving members 122.

Each of the plurality of the activation members 101 and the first gear 102 is rotatable about a rotational axis extending in a direction perpendicular to a surface of a base 16, that is, extending in the X-axis direction. The second gear 103 is rotatable about a rotational axis extending in the longitudinal direction of the shaft 12, that is, extending in the Z-axis direction. The shaft 12 engages with the second gear 103, and rotates in the directions indicated by the arrows A in conjunction with the rotation of the second gear 103.

The actuator receives the control signal from the patient-side apparatus 1 illustrated in FIG. 1 via the manipulator 3. Based on this control signal, the actuator rotates the plurality of transmission members. The rotation of each transmission member causes an associated one of the plurality of activation members 101 and the first gear 102 to rotate.

More specifically, the activation mechanism 15 has three activation members 101. The three activation members 101 will be referred to as activation members 101A, 101B, and 101C. The activation members 101A, 101B, and 101C are inserted, for example, in a plurality of through holes (not shown) formed in the base 16. The wires 141, 142, and 143 illustrated in FIG. 5 are wound around the activation members 101A, 101B, and 101C, respectively.

When the rotation, by the actuator, of the transmission member associated with the activation member 101A causes the activation member 101A to rotate, the wire 141 wound around the activation member 101A moves along the Z-axis. Consequently, the finger portion 24b illustrated in FIG. 3 pivots in the directions indicated by the arrows C.

When the rotation, by the actuator, of the transmission member associated with the activation member 101B causes the activation member 101B to rotate, the wire 142 wound around the activation member 101B moves along the Z-axis. Consequently, the finger portion 24a illustrated in FIG. 3 pivots in the directions indicated by the arrows C.

When the rotation, by the actuator, of the transmission member associated with the activation member 101C causes the activation member 101C to rotate, the wire 143 wound around the activation member 101C moves along the Z-axis. Consequently, the wrist portion 23 illustrated in FIG. 3 pivots in the directions indicated by the arrows B.

When the rotation, by the actuator, of the transmission member associated with the first gear 102 causes the first gear 102 to rotate, the second gear 103 engaged with the first gear 102 rotates about the rotational axis extending in the Z-axis direction. Consequently, the shaft 12 rotates in the directions indicated by the arrows A in conjunction with the rotation of the second gear 103. Detailed configurations of the activation member 101 will be described below.

[Activation Member]

Figure 7:
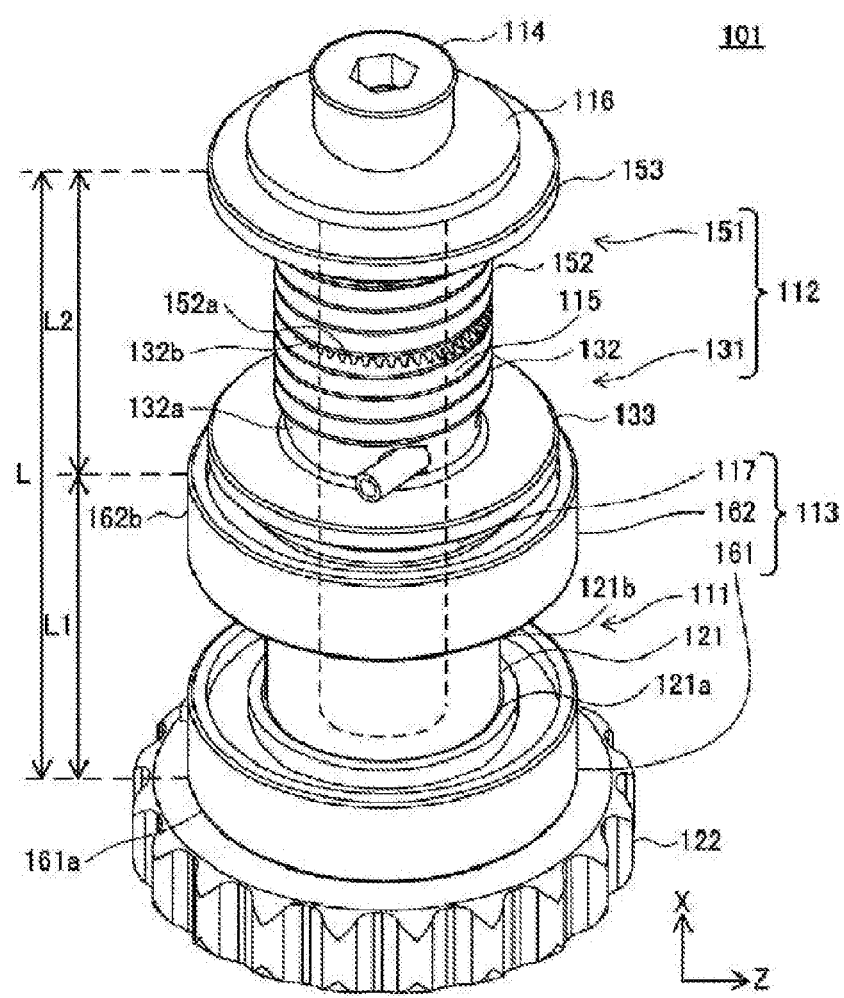
FIG. 7 is a diagram illustrating a perspective view of a configuration of an activation member of the activation mechanism in FIG. 6.
Figure 8:
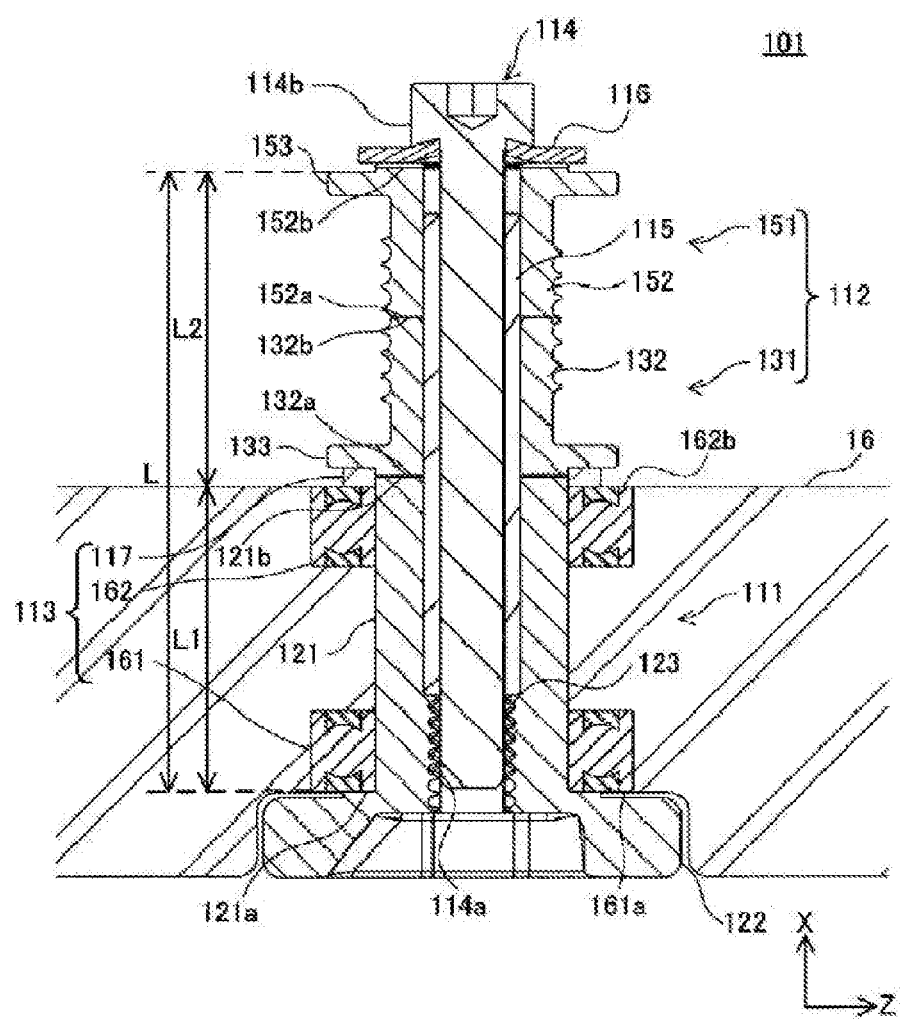
FIG. 8 is a diagram illustrating a cross-sectional view of the configuration of the activation member in FIG. 7.

FIG. 7 is a diagram illustrating a perspective view of a configuration of an activation member of the activation mechanism in FIG. 6. FIG. 8 is a diagram illustrating a cross-sectional view of the configuration of the activation member in FIG. 7.

Referring to FIGS. 7 and 8, the activation member 101 has a rotation portion (i.e., a first rotation member) 111 attached to the base 16, a pulley portion 112 which includes a first pulley portion (i.e., a second rotation member) 131 and a second pulley portion (i.e., a third rotation member) 151, a bearing portion 113, a pressing member 114, a rod-shaped hollow member 115, and a spring washer 116 arranged between the pressing member 114 and the pulley portion 112. Configuration of the respective members will be described below.

(Rotation Portion and Pulley Portion)

Figure 9:
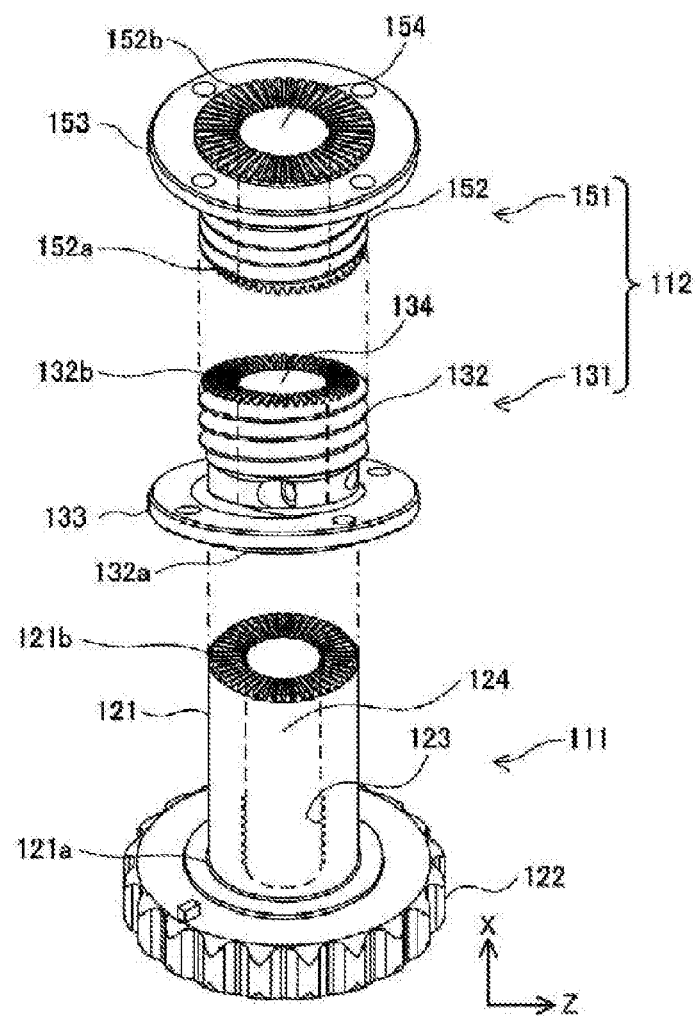
FIG. 9 is a diagram illustrating perspective views of configurations of a rotation portion and a pulley portion of the activation member in FIG. 7.

FIG. 9 is a diagram illustrating perspective views of configurations of the rotational portion and the pulley portion of the activation member in FIG. 7. In this embodiment, the X-axis direction corresponds to a vertical direction. The upward direction is the positive direction of the X-axis, and the downward direction is the negative direction of the X-axis.

Referring to FIG. 9, the rotation portion 111 has a cylindrical portion 121 and a receiving member 122 coupled to a lower end 121a of the cylindrical portion 121. The receiving member 122 engages with a transmission member. The rotation of the receiving member 122 caused by the rotation of the transmission member causes the entire activation member 101 to rotate about the rotational axis.

The cylindrical portion 121 is provided with radially extending ridges and grooves in its upper end 121b, which is opposite to the end where the receiving member 122 is coupled. That is, the upper end 121b of the cylindrical portion 121 is configured as a face gear.

The cylindrical portion 121 is also provided, inside thereof, with an insertion hole 124 extending parallel to the rotational axis of the rotation portion 111, that is, in the vertical direction. Part of the inner surface of the cylindrical portion is provided with an engaging groove 123.

For example, the first and second pulley portions 131 and 151 are formed into the same shape, and attached to each other so as to be oppositely oriented in the vertical direction. The first and second pulley portions 131 and 151 having the same shape can facilitate the production and reduce the cost.

More specifically, the first pulley portion 131 has a first pulley's cylindrical portion 132 and a first pulley's flange portion 133 coupled to a vicinity of a lower end 132a of the first pulley's cylindrical portion 132. The first pulley's cylindrical portion 132 is provided with ridges and grooves in a surface of the lower end 132a and a surface of an upper end 132b. That is, the lower and upper ends 132a and 132b of the first pulley's cylindrical portion 132 are configured as face gears. The outer circumferential surface of the first pulley's cylindrical portion 132 is provided with ridges and grooves having a helical structure. A wire 14 is wound around the ridges and grooves.

The first pulley's cylindrical portion 132 is also provided with an insertion hole 134 extending parallel to the rotational axis of the first pulley portion 131, that is, in the vertical direction.

Similarly to the first pulley portion 131, the second pulley portion 151 has a second pulley's cylindrical portion 152 and a second pulley's flange portion 153 coupled to a vicinity of an upper end 152b of the second pulley's cylindrical portion 152. The second pulley's cylindrical portion 152 is provided with ridges and grooves in a surface of a lower end 152a and a surface of the upper end 152b. That is, the lower and upper ends 152a and 152b of the second pulley's cylindrical portion 152 are configured as face gears. The outer circumferential surface of the second pulley's cylindrical portion 152 is provided with ridges and grooves having a helical structure. The wire 14 is wound around the ridges and grooves.

The second pulley's cylindrical portion 152 is also provided with an insertion hole 154 extending parallel to the rotational axis of the second pulley portion 151, that is, in the vertical direction.

The insertion hole 134 of the first pulley's cylindrical portion 132, the insertion hole 154 of the second pulley's cylindrical portion 152, and the insertion hole 124 of the cylindrical portion 121 of the rotation portion 111 have substantially the same diameter.

The ridges and grooves formed in the upper end 121b of the rotation portion 111 engage with the ridges and grooves formed in the lower end 132a of the first pulley portion 131. The ridges and grooves formed in the upper end 132b of the first pulley portion 131 engage with the ridges and grooves formed in the lower end 152a of the second pulley portion 151.

(Bearing Portion)

As illustrated in FIGS. 7 and 8, the hearing portion 113 has a lower bearing 161, an upper bearing 162, and a washer 117. The lower and upper bearings 161 and 162 are mounted on the outer circumferential surface of the cylindrical portion 121 of the rotation portion 111. That is, the rotation portion 111 can rotate smoothly since the rotation portion 111 is attached to the base 16 via the lower bearing 161 or the upper bearing 162.

The washer 117 is disposed between the upper bearing 162 and the first pulley's flange portion 133 of the first pulley portion 131. Typical bearings can be used as the lower and upper bearings 161 and 162. Those bearings which will be described below may also be employed.

Figure 10:
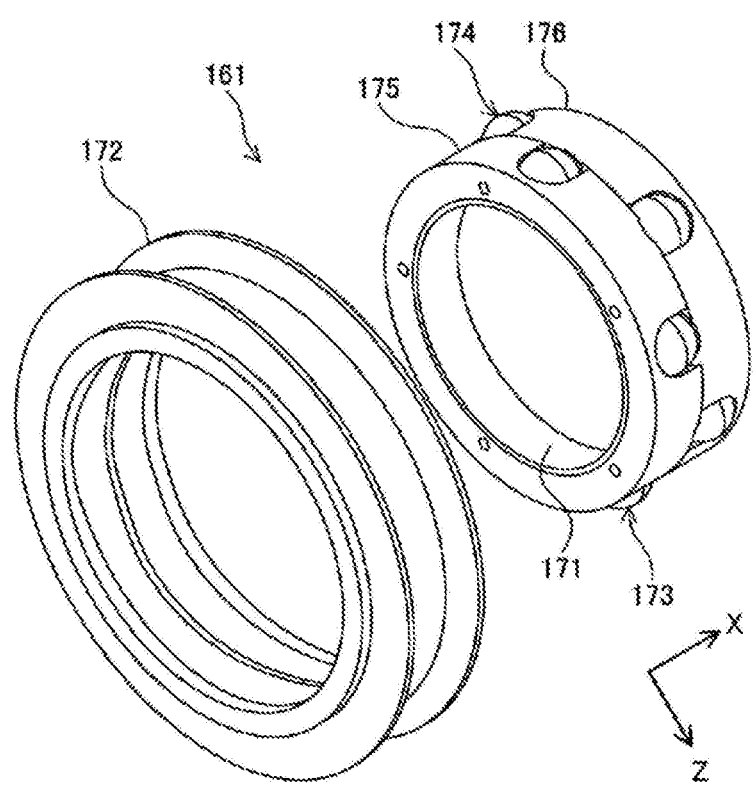
FIG. 10 is a diagram illustrating exploded perspective views of configurations of a lower bearing and an upper bearing in FIG. 7.

FIG. 10 is a diagram illustrating exploded perspective views of configurations of the lower bearing and the upper bearing in FIG. 7. A configuration of the lower bearing 161 will be described in this embodiment. The upper bearing 162 is configured similarly to the lower bearing 161.

The lower bearing 161 has an inner ring member 71, an outer ring member 172, a first ball group 173 having a plurality of balls, a second ball group 174 having a plurality of balls, a first retainer 175, and a second retainer 176. The inner ring member 171, the outer ring member 172, the first retainer 175, and the second retainer 176 have a ring shape.

The inner diameter of the outer ring member 172 is larger than the outer diameter of the inner ring member 171. The outer ring member 172 accommodates the inner ring member 171 therein such that the central axes of the outer and inner ring members 172 and 171 are aligned with each other.

The plurality of balls of the first ball group 173 are accommodated in the first retainer 175, where the balls are arranged at regular intervals in the circumferential direction of the first retainer 175. The plurality of balls of the second ball group 174 are accommodated in the second retainer 176, where the balls are arranged at regular intervals in the circumferential direction of the second retainer 176.

The number of balls of the first ball group 173 and the number of balls of the second ball group 174 are the same. Each ball has the same size. The first and second retainers 175 and 176 have the same shape. The first and second retainers 175 and 176 are brought into contact with each other, with the central axes thereof aligned with each other, and are disposed between the inner and outer ring members 171 and 172.

The lower bearing 161 may be configured such that the first retainer 175 or the second retainer 176 is provided. In other words, the retainer may be provided in a single line. However, the configuration in which the retainers are provided in double lines described above can disperse the load, applied to the retainers due to the rotation of the activation member 101, more than the configuration in which the retainer is provided in a single line. Consequently, the durability of the lower bearing 161 can be improved, and the medical treatment tool 4b can be used more times and for a longer period of time.

The balls of the first ball group 173 and the balls of the second ball group 174 are alternately arranged in the circumferential direction of the first and second retainers 175 and 176. Part of each ball of the first ball group 173 is accommodated in the second retainer 176. Part of each ball of the second ball group 174 is accommodated in the first retainer 175.

This configuration can keep the width of the lower bearing 161 in the X-axis direction from increasing. It is thus possible to prevent an increase in the friction at a contact portion between the rotation portion 111 and the lower bearing 161 attached to the rotation portion 111.

(Attachment Position of Bearing Portion)

Referring again to FIGS. 7 and 8, for example, the lower bearing 161 is attached to a vicinity of the lower end 121a of the cylindrical portion 121, and the upper bearing 162 is attached to a vicinity of the upper end 121b of the cylindrical portion 121. The length of the bearing portion 113 in the X-axis direction (i.e., the length L1 in the X-axis direction from the lower end 161a of the lower bearing 161 to the upper end 162b of the upper bearing 162) is relatively long with respect to the whole size of the activation member 101. Thus, the length L1 in the X-axis direction from the lower end 161a of the lower bearing 161 to the upper end 162b of the upper bearing 162 is about the same as the length of the cylindrical portion 121 of the rotation portion 111.

More specifically, the length in the X-axis direction from the upper end 162b of the upper bearing 162 to an upper end of the second pulley's flange portion 153 of the second pulley portion 151 (i.e., about the same length as the pulley portion 112) is referred to as a length L2. The sum of the lengths L1 and L2 is referred to as a length L. In this case, the length L1 is longer than or equal to one fourth (i.e., ¼) of the length L.

The length L1 is preferably longer than or equal to one third (i.e., ⅓) of the length L, and more preferably approximately a half (i.e., ½) of the length L. The approximately half (½) of the length L falls within a range between, for example, (L×½) and (L×½±L×0.1).

Specifically, the lengths L1, L2, and L have the following lengths: L1=9.5 mm; L2=9.8 mm; and L=19.3 mm. The activation member 101 may be configured to satisfy, for example, L1=6.4 mm, L2=12.9 mm, and L=19.3 mm so that the length L1 is slightly shorter than one third (i.e., ⅓) of the length L.

In known techniques, for example, in order to rotatably mount the activation member 101 firmly enough to activate the elongate element 14, the activation member 101 is secured to a support member, such as one indicated at "138" in FIG. 22 of Patent Document 1, with bearings provided on both of the upper and lower sides of the activation member 101.

On the other hand, the activation member 101 according to one or more embodiments is configured such that the lower and upper bearings 161 and 162 are attached to the lower end 121a and the upper end 121b of the cylindrical portion 121 of the rotation portion 111, respectively.

As mentioned earlier, the length L1 from the lower end 161a of the lower bearing 161 to the upper end 162b of the upper bearing 162 is relatively long, that is, longer than or equal to one fourth (i.e., ¼) of the length L. Thus, the lower and upper bearings 161 and 162 can support the activation member 101 without tilting and backlash of the activation member 101.

It is therefore not necessary to provide a support member near the upper end 152b of the second pulley portion 151, which contributes to reducing the size and weight of the activation mechanism 15. The reduction in size and weight if the activation mechanism 15 contributes to reducing the size and weight of the medical treatment tool 4b.

The locations where the lower and upper bearings 161 and 162 are attached are not limited to those locations described above. The configuration of the bearing portion 113 is not limited to the configuration having the lower and upper bearings 161 and 162. The bearing portion 113 may have one bearing or three or more bearings.

(Pressing Member and Hollow Member)

As illustrated in FIG. 8, the pressing member 114 and the hollow member 115 are accommodated in the pulley portion 112 and the rotation portion 111.

More specifically, the length of the hollow member 115 in the X-axis direction is longer than or equal to the length L2 and shorter than the length L. The hollow member 115 is inserted in the insertion hole 124 of the rotation portion 111, the insertion hole 134 of the first pulley portion 131, and the insertion hole 154 of the second pulley portion 151. The outer diameter of the hollow member 115 is slightly smaller than the diameters of the insertion holes 124, 134, and 154.

The pressing member 114 is, for example, a screw or a bolt. The length of the pressing member 114 is longer than or equal to the length L2 and shorter than the length L, and is longer than the hollow member 115. The pressing member 114 is provided with an engaging groove 114a near the lower end thereof, and a flange portion 114b coupled to the upper end, which is opposite to the end where the engaging groove 114a is provided. The engaging groove 114a is, for example, a screw thread having a helical structure.

The pressing member 114 is inserted in the insertion hole 124 of the rotation portion 111, the insertion hole 134 of the first pulley portion 131, and the insertion hole 154 of the second pulley portion 151. More specifically, the pressing member 114 is accommodated in the hollow member 115 inserted in the insertion holes 124, 134, and 154, with the spring washer 116 interposed between the pressing member 114 and an upper end 152b of the second pulley's cylindrical portion 152. The end portion where the engaging groove 114a is formed sticks out of the hollow member 115.

The diameter of the pressing member 114 is determined such that the pressing member 114 is rotatable in the hollow member 115. The engaging groove 114a of the pressing member 114 engages with the engaging groove 123 formed in the inner surface of the rotation portion 111. In this configuration, the flange portion 114b of the pressing member 114 presses the rotation portion 111 and the pulley portion 112, with the spring washer 116 interposed therebetween, in an extending direction of the rotational axis, that is, downward.

With the pressing member 114 pressing the rotation portion 111 and the pulley portion 112 downward, the state of engagement between the face gears of the rotation portion 111 and the first pulley portion 131 and the state of engagement between the face gears of the first pulley portion 131 and the second pulley portion 151 are fixed.

In known techniques, in order to fix the wire 14 to the pulley portion 112 while keeping tension on the wire 14, a member, such as the annular collar indicated at "178" or "180" in FIG. 23 of Patent Document 1 is employed to screw the wire 14 to the shaft.

On the other hand, the activation member 101 according to one or more embodiments is configured such that the face gear of the pulley portion 112, around which the wire 14 is wound while keeping tension on the wire 14, is engaged with the face gear of the rotation portion 111. This configuration does not require a screw or the like for fixing the pulley portion 112 to the rotation portion 111. It is therefore not necessary to provide a portion that receives the screw, which contributes to reducing the size and weight of the activation mechanism 15. The reduction in size and weight of the activation mechanism 15 contributes to reducing the size and weight of the medical treatment tool 4b.

With this configuration, the state of engagement between the rotation portion 111 and the first pulley portion 131 and the state of engagement between the first pulley portion 131 and the second pulley portion 151 are more firmly fixed than in the case where a screw or the like is used to fix the pulley portion 112. It is therefore possible to improve the durability and safety of the medical treatment tool 4b.

[Method for Fabricating Activation Mechanism]

Figure 11:
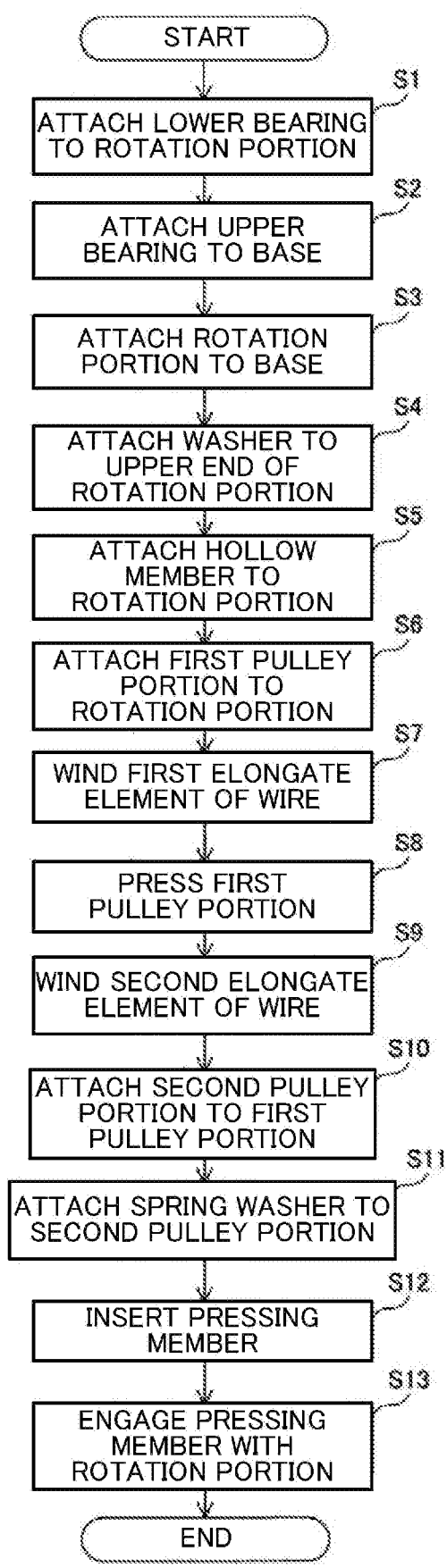
FIG. 11 is an example flowchart showing steps of a method for fabricating the activation mechanism of one or more embodiments.

FIG. 11 is an example flowchart showing steps of a method for fabricating the activation mechanism of one or more embodiments. Steps of a method for fabricating the activation member 101 around which the wire 14 is wound will be described herein. The wires 142 and 143 are wound around the respective activation members 101 according to the similar steps.

Referring to FIG. 11, a worker first attaches the lower bearing 161 to the lower end 121a of the cylindrical portion 121 of the rotation portion 111 (step S1). The worker then attaches the upper bearing 162 to the base 16 (step S2).

Next, the worker inserts the cylindrical portion 121 in a through hole formed in the base 16, thereby attaching the rotation portion 111 to the base 16 via the lower and upper bearings 161 and 162 (step S3).

Next, the worker attaches the washer 117 to the upper end 121b of the cylindrical portion 121 of the rotation portion 111 (step S4).

Next, the worker aligns the rotational axis of the rotation portion 111 with the central axis of the hollow member 115, and inserts the hollow member 115 in the insertion hole 124 of the rotation portion 111, thereby attaching the hollow member 115 to the rotation portion 111 (step S5).

Next, the worker aligns the central axis of the hollow member 115 and the central axis of the first pulley portion 131, and inserts the hollow member 115 in the insertion hole 134 of the first pulley portion 131, thereby attaching the first pulley portion 131 to the rotation portion 111 (step S6).

Next, the worker winds the first elongate element 141a of the wire 141 around the outer circumferential surface of the first pulley portion 131 (step S7). The worker then presses the first pulley portion 131, while maintaining engagement between the ridges and grooves formed at the lower end 132a of the first pulley portion 131, around which the first elongate element 141a of the wire 141 is wound, and the ridges and grooves formed at the upper end 121b of the rotation portion 111 (step S8). Pressing in this manner can keep the first pulley portion 131 from rotating about its rotational axis.

Next, the worker, while winding the second elongate element 141b of the wire 141 around the second pulley portion 151 (step S9), aligns the central axis of the hollow member 115 and the central axis of the second pulley portion 151, and attaches the second pulley portion 151 to the first pulley portion 131 such that the hollow member 115 passes through the insertion hole 154 of the second pulley portion 151 (step S10). The worker then engages the ridges and grooves formed at the lower end 152a of the second pulley portion 151, around which the second elongate element 141b of the wire 141 is wound, with the ridges and grooves formed at the upper end 132b of the first pulley portion 131.

The engagement between the face gear of the rotation portion 111 and the face gear of the first pulley portion 131, and the engagement between the face gears of the first and second pulley portions 131 and 151 can keep the first and second pulley portions 131 and 151 from making an unintentional rotation. This configuration can facilitate the assembly while keeping tension on the wire 141, without the need to provide a member such as a screw.

The worker then attaches the spring washer 116 to the second pulley portion (step S11). Next, the worker inserts the pressing member 114 in the hollow member 115 with the spring washer 116 interposed therebetween. At this moment, the engaging groove 114a formed at the end portion of the pressing member 114 sticks out of the hollow member 115 (step S12).

The worker then rotates the pressing member 114 in the hollow member 115 to engage the engaging groove 114a of the pressing member 114 with the engaging groove 123 of the rotation portion 111. That is, the worker screws the pressing member 114 to the rotation portion 111 (step S13). With the pressing member 114 pressing the rotation portion 111 and the pulley portion 112 downward in this manner, the state of engagement between the rotation portion 111 and the first pulley portion 131 and the state of engagement between the first pulley portion 131 and the second pulley portion 151 are fixed.

In this state, the spring washer 116 is pressed downward by the pressing member 114, and presses the pressing member 114 upward due to its own resilience. Thus, the state of engagement between the rotation portion 111 and the first pulley portion 131 and the state of engagement between the first pulley portion 131 and the second pulley portion 151 are fixed more firmly.

Note that the method for fabricating the activation member is not limited to those steps described above. For example, the washer 117 may be attached (step S4) after the hollow member 115 is attached (step S5). For example, the hollow member 115 may be attached (step S5) after the second pulley portion 151 is attached (step S10).

The activation member 101 illustrated in FIGS. 7 and 8 may be configured without the hollow member 115. However, the activation member 101 provided with the hollow member 115 allows the first and second pulley portions 131 and 151 to rotate at fixed positions on the hollow member 115, during winding of the first elongate element 141a around the first pulley portion 131 and during winding of the second elongate element 141b around the second pulley portion 151. The workability can therefore be improved.

The pulley portion 112 is not limited to a configuration having a plurality of members. That is, the first pulley portion (i.e., the second rotation member) 131 and the second pulley portion (i.e., the third rotation member) 151 may be integrally formed. However, the first and second pulley portions 131 and 151 formed independently of each other allow the first and second elongate elements 141a and 141b of the wire 141 to be wound around a plurality of different rotation members. The rotation members can be rotated in opposite directions, thereby making it possible to easily adjust the tension of the wire 141.

The rotation portion 111 and the first and second pulley portions 131 and 151 may be integrally formed. The rotation portion 111 and the first pulley portion 131 may be integrally formed. However, the activation member 101 configured as being separable in the X-axis direction, that is, the rotation portion 111 and the first pulley portion 131 formed independently of each other, allows for easy insertion of a tool, used to form the engaging groove 123, into the rotation portion 111. This configuration can facilitate the formation of the engaging groove 123.

The pressing member 114 may engage with the pulley portion 112 instead of engaging with the rotation portion 111. However, the cylindrical portion 121 of the rotation portion 111 has a larger outer diameter than the first pulley's cylindrical portion 132 and the second pulley's cylindrical portion 152 included in the pulley portion 112. That is, the cylindrical portion 121 is thicker than the first pulley's cylindrical portion 132 and the second pulley's cylindrical portion 152. Thus, the configuration in which the pressing member 114 engages with the thick rotation portion 111, as mentioned above, can provide more durability to the engaged portion than a configuration in which the pressing member 114 engages with the pulley portion 112.

[Transmitted Member]

As mentioned earlier, the transmitted member 122 for the rotation portion 111 of the activation member 101 engages with the transmission member and rotates together with the transmission member. Detailed configuration of the portion where the transmitted member 122 engages with the transmission member will be described below.

Figure 12:
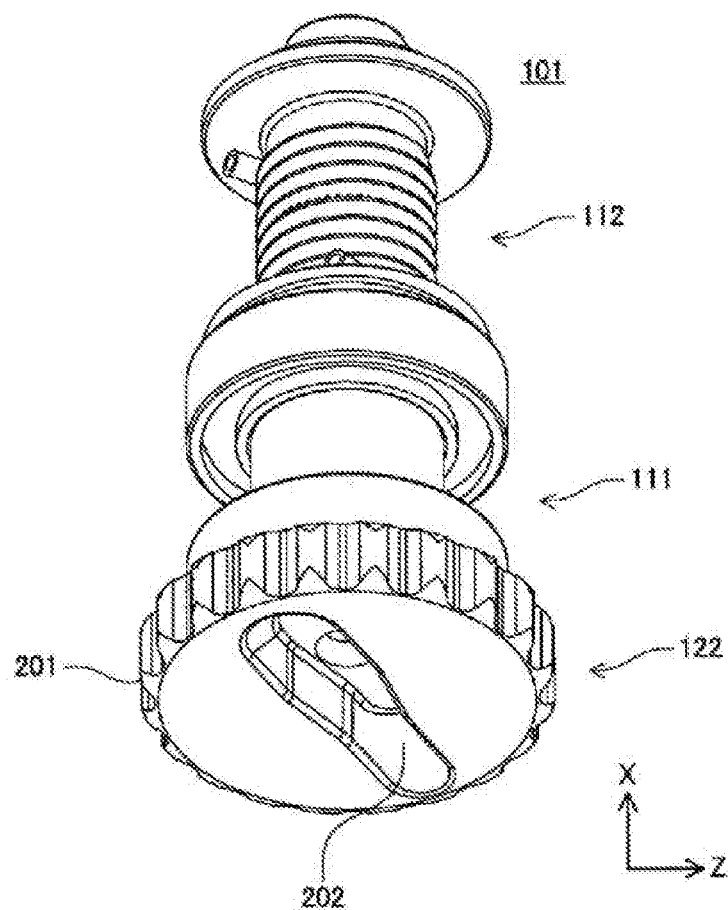
FIG. 12 is a diagram illustrating a perspective view of a configuration of a receiving member for the activation member of one or more embodiments.
Figure 13:
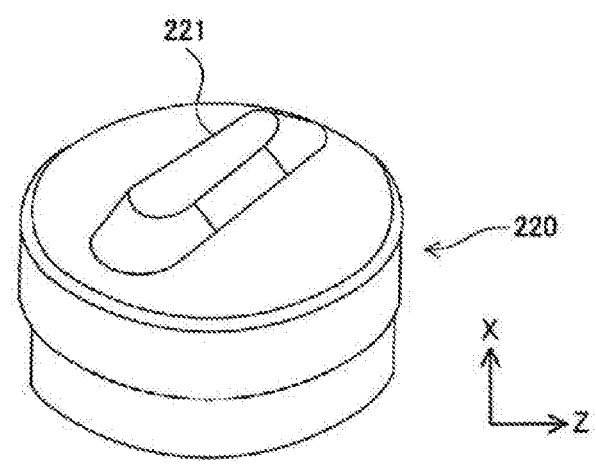
FIG. 13 is a diagram illustrating a perspective view of a configuration of a transmission member which engages with the receiving member in FIG. 12.

FIG. 12 is a diagram illustrating a perspective view of a configuration of a transmitted member for the activation member of one or more embodiments. FIG. 13 is a diagram illustrating a perspective view of a configuration of a transmission member which engages with the transmitted member in FIG. 12.

Referring to FIG. 12, the rotation portion 111 of the activation member 101 has the transmitted member 122 that engages with the transmission member 220, as mentioned earlier. The transmitted member 122 has a rotatable disc portion 201. An engaged portion 202 is formed in a main surface of the disc portion 201. The transmission member 220 has an engaging portion 221 engageable with the engaged portion 202 of the transmitted member 122.

The engaged portion 202 of the transmitted member 122 is, for example, a groove or an indentation which, on the main surface of the disc portion 201, is asymmetric with respect to all straight lines passing through the center of said main surface, and has a continuous shape. The engaging portion 221 of the transmission member 220 is, for example, a projection which, on a main surface of the transmission member 220, is asymmetric with respect to all straight lines passing through the center of said main surface, and has a continuous shape, similarly to the engaged portion 202.

Thus, the orientation of the transmitted member 122 for activating the end portion 11 as illustrated in FIG. 2 can be fixed at one specific position within 360 degrees.

Suppose that the transmitted member 122 is provided with a groove or an indentation in a symmetric shape with respect to a straight line passing through the center of the main surface of the disc portion 201, and that the transmission member 220 is provided with a projection in a symmetric shape with respect to a straight line passing through the center of the main surface of the transmission member 220. In this case, the orientation of the transmitted member 122 relative to the transmission member 220 is not fixed at one specific position, and even if the transmitted member 122 rotates 180 degrees, the transmitted member 122 can still engage with the transmission member 220. The transmitted member 122 which has rotated 180 degrees but still engages with the transmission member 220 at that position results in an unintended movement of the end portion 11.

To avoid this, the orientation of the transmitted member 122 needs to be fixed at one specific position within 360 degrees. In the embodiment of one or more embodiments, the transmitted member 122 is provided with a groove or an indentation that is asymmetric with respect to all straight lines passing through the center of the main surface of the disc portion 201, and the transmission member 220 is provided with a projection asymmetric with respect to all straight lines passing through the center of the main surface of the transmission member 220.

The transmission member 220, in its initial state before the start of surgery, is disposed such that the engaging portion 221 on the main surface thereof is directed in a predetermined direction. The worker rotates the rotation portion 111 about the rotational axis of the rotation portion 111 so that the orientation of the engaged portion 202 is aligned with the orientation of the engaging portion 221. The worker then engages the engaging portion 221 with the engaged portion 202, while maintaining the orientation of the engaging portion 221 aligned with the orientation of the engaged portion 202.

At the time of fabrication, the orientations of the respective engaged portions 202 of the plurality of transmitted members 122 are adjusted such that the engaged portions 202 are oriented in the same direction in a state in which the end portion 11 takes a general position, such as the positions illustrated in FIGS. 3 and 4.

The engaging portion 221 and the engaged portion 202 have a linear shape, for example. Further, for example, the engaging portion 221 is in a shape which passes through the center of the main surface of the transmission member 220, and the engaged portion 202 is in a shape which passes through the center of the main surface of the disc portion 201.

The engaging portion 221 is configured such that the width thereof gradually decreases toward the transmitted member 122 (i.e., upward) in the X-axis direction orthogonal to the main surface of the transmission member 220. The engaged portion 202 is configured such that the width thereof gradually increases toward the transmission member 220 (i.e., downward) in the X-axis direction orthogonal to the main surface of the disc portion 201. In other words, the engaging portion 221 and the engaged portion 202 are tapered.

The transmission member 220 is biased toward the transmitted member 122, that is, toward the positive direction of the X-axis illustrated in FIG. 13, by a spring or the like. Thus, even if there is a small misalignment between the engaged portion 202 and the engaging portion 221, such a misalignment is corrected at the time of attachment, and the engaging portion 221 is fitted in the engaged portion 202. This configuration can simplify a step of engaging the engaging portion 221 with the engaged portion 202.

The engaging portion 221 may be configured as a groove or an indentation, instead of being configured as the projection. In the case in which the engaging portion 221 is a groove or an indentation, the engaged portion 202 is configured as a projection engageable with the engaging portion 221.

Further, the shape of the engaged portion 202 is not limited to the shape described above, as long as the engaged portion 202 is asymmetric, on the plane of rotation of the disc portion 201, with respect to all straight lines passing through the center of the disc portion 201, and has a continuous shape. For example, the engaged portion 202 may have a shape other than a linear shape. Further, for example, the engaged portion 202 may have a shape that does not pass through the center of the disc portion 201. For example, the engaged portion 202 may have a shape like the letter "V" in English.

Further, the engaging portion 221 and the engaged portion 202 do not have to come into direct contact with each other to transmit the rotation of the transmission member 220 to the transmitted member 122. For example, the rotation of the transmission member 220 may be transmitted to the transmitted member 122 via an adopter. In such a case, the adopter has a disc which includes two surfaces. One surface is provided with an engaged portion which is engaged with the engaging portion 221. The other surface is provided with an engaging portion which engages with the engaged portion 202.

The features described in this section can be summarized as follows.

[1] A transmitted member engaged with a transmission member which transmits a rotation caused by an actuator to a rotation member, wherein the transmitted member includes a rotatable disc portion and an engaged portion formed at a surface of the disc portion; and the engaged portion is a projection, a groove, or an indentation that is asymmetric with respect to all straight lines passing through a center of the disc portion, and has a continuous shape.

[2] The transmitted member in item [1], wherein the continuous shape is a linear shape.

[3] The transmitted member in item [1] or [2], wherein the continuous shape passes through the center of the disc portion.

[4] The transmitted member in any one of items [1] to [3], wherein the engaged portion is a groove or an indentation, and is configured such that a width of the engaged portion increases toward the transmission member in a direction orthogonal to the surface.

[5] The transmitted member in any one of items [1] to [4], wherein the engaged portion is a projection, and is configured such that the width of the engaged portion decreases toward the transmission member in the direction orthogonal to the surface.

[6] An activation force transmission system including the transmitted member of any one of items [1] to [5] and the transmission member including an engaging portion which engages with the engaged portion.

The embodiment disclosed herein is meant to be illustrative in all respects and should not be construed to be limiting in any manner. The scope of one or more embodiments is defined not by the above description, but by the scope of claims, and intended to include all modifications within equivalent meaning and scope to those of the claims.

What is claimed is:

1. An activation member around which an elongate element is wound,
    the activation member comprising:
    a plurality of rotation members rotatable about a rotational axis and comprising a first rotation member and a second rotation member; and
    a pressing member which engages with at least one of the plurality of rotation members,
    the first rotation member and the second rotation member respectively include surfaces opposed to each other in a direction of the rotational axis such that each of the opposed surfaces includes a face gear, wherein
    the first rotation member and the second rotation member are engaged with each other via the face gears by being pressed in the direction of the rotational axis by the pressing member.

2. The activation member of claim 1, further comprising:
    a bearing portion, wherein
    at least one of the plurality of rotation members is attached to a base via the bearing portion.

3. The activation member of claim 2, wherein
    the bearing portion includes a plurality of bearings.

4. The activation member of claim 1, wherein
    each of the plurality of rotation members is provided with an insertion hole extending parallel to the rotational axis, and
    the pressing member is a screw or a bolt inserted in the insertion hole of each of the rotation members.

5. The activation member of claim 1, further comprising:
    a hollow member provided between the plurality of rotation members and the pressing member.

6. The activation member of claim 1, further comprising:
    a transmitted member engaged with a transmission member which transmits a rotation caused by an actuator to the plurality of rotation members, wherein the transmitted member includes a disc portion rotatable about the rotational axis, the disc portion has a surface provided with an engaged portion, and the engaged portion is a projection, a groove, or an indentation that is asymmetric with respect to all straight lines passing through a center of the disc portion, and has a continuous shape.

7. A medical treatment tool configured to be detachable from a manipulator, comprising:

an end portion;

a shaft supporting the end portion at a distal end of the shaft;

an elongate element; and an activation mechanism activating the elongate element to operate the end portion, wherein the activation mechanism comprises a base and an activation member, the activation member comprises:

a plurality of rotation members rotatable about a rotational axis and comprising a first rotation member and a second rotation member; and a pressing member which engages with the first rotation member to integrally attach the plurality of rotation members to the base, the first rotation member and the second rotation member respectively include surfaces opposed to each other in a direction of the rotational axis such that each of the opposed surfaces includes a face gear, and the first rotation member and the second rotation member are engaged with each other via the face gears by being pressed in the direction of the rotational axis by the pressing member.

8. The medical treatment tool of claim 7, wherein the plurality of rotation members comprises a cylindrical portion, the cylindrical portion and the second rotation member respectively include surfaces opposed to each other in the direction of the rotational axis such that each of the opposed surfaces includes a face gear, wherein the cylindrical portion and the second rotation member are engaged with each other via the face gears by being pressed in the direction of the rotational axis by the pressing member.

9. The medical treatment tool of claim 8, wherein the cylindrical portion is rotatably attached to the base via a bearing portion.

10. The medical treatment tool of claim 7, further comprising a transmitted member detachably engaged with a transmission member which is included in the manipulator and transmits a rotation caused by an actuator included in the manipulator to the rotation members, wherein the transmitted member includes a disc portion rotatable about the rotational axis, the disc portion has a surface provided with an engaged portion, and the engaged portion comprises a projection, a groove, or an indentation.

11. The medical treatment tool of claim 7, wherein the end portion includes a wrist portion pivotally mounted on the distal end of the shaft.

12. The medical treatment tool of claim 11, further comprising a second elongate element; and a second activation mechanism which activates the second elongate element to operate the wrist portion, wherein the second activation mechanism comprises a second activation member, the second activation member comprising:

a plurality of rotation members rotatable about a second rotational axis and comprising a third rotation member and a fourth rotation member; and a second pressing member which engages with the third rotation member to integrally attach the plurality of rotation members of the second activation member to the base, the third rotation member and the fourth rotation member respectively include surfaces opposed to each other in a direction of the second rotational axis such that each of the opposed surfaces thereof includes a face gear, and the third rotation member and the fourth rotation member are engaged with each other via the face gears thereof by being pressed in the direction of the second rotational axis by the second pressing member.

* * * * *